United States Patent [19]

Oh

[11] Patent Number: 4,537,712
[45] Date of Patent: Aug. 27, 1985

[54] NON-SPECIFIC SUPPRESSIVE FACTORS AND PROCESS

[75] Inventor: Se-Kyung Oh, Brookline, Mass.

[73] Assignee: Trustees of Boston University, Boston, Mass.

[21] Appl. No.: 533,065

[22] Filed: Sep. 19, 1983

Related U.S. Application Data

[63] Continuation of Ser. No. 325,710, Nov. 30, 1981, abandoned.

[51] Int. Cl.$^3$ ............................................. C07G 7/00
[52] U.S. Cl. ........................... 260/112 R; 260/112 B; 424/101; 514/2
[58] Field of Search ...................... 260/112 R, 112 B; 424/101, 177

[56] References Cited

PUBLICATIONS

Oh et al., Fed. Proc. 39 (3) Abstract #4719, 1980.

Nelken et al., J. Immunological Methods, vol. 28, pp. 267–276, 1979.

Primary Examiner—John Kight
Assistant Examiner—Garnette D. Draper
Attorney, Agent, or Firm—Paul J. Cook; Lawrence Gilbert

[57] ABSTRACT

A high purity immunosuppression factor (IF) having a molecular weight of about 50,000 or a reduced IF having a molecular weight of about 25,000 derived from the higher molecular weight IF and which is stable in dilute aqueous solutions is obtained from human ascites fluid. An extract of human ascites fluid is subjected to chromatography to recover a component of the ascites fluid rich in the immunosuppression factor and containing proteinaceous material which does not degrade the IF factor. The pure IF is obtained by subjecting the component rich in IF to contact with solid phase anti-human IgG (Fc specific) to recover pure IF having a molecular weight of above 50,000. The reduced IF is obtained by heating the higher molecular weight IF.

1 Claim, 6 Drawing Figures

NON-SPECIFIC SUPPRESSIVE FACTORS AND PROCESS

This is a continuation of application Ser. No. 325,710 filed Nov. 30, 1981, now abandoned.

BACKGROUND OF THE INVENTION

This invention relates to purified non-specific suppression factor and to a process for isolating the same.

A degree of immunosuppression commonly accompanies a variety of virus-induced tumors, chemically induced tumors, experimental amyloidosis, liver cirrhosis, infection and pregnancy. The precise mechanism is not known, but numerous reports indicate that non-cytotoxic immunosuppressive humoral factors in normal or malignant serum may play a role. Unlike the serum-blocking factors that contain specific antibodies to tumor associated antigens, the non-specific suppressive factors inhibit responses to a spectrum of unrelated antigens. The cellular origin of these factors is not known. It has been shown that malignant ascites fluids are abundant sources of these factors and that tumor extracts also contain non-specific suppressive factors. It also has been shown that the suppressive factors in malignant human ascites fluids (three ovarian and two colonic cancer ascites fluids) exist as macromolecular complexes and that the active component can be extracted and purified as a smaller M.W. (50,000), potent immunosuppressive moiety (Oh et al, Fed. Proc. 39:1614). This was shown to suppress T-dependent antibody responses in vivo and T-dependent mitogen responses in vitro at microgram concentrations per ml. This suppressive factor could not be identified with any of the plasma proteins.

It would be desirable to provide purified non-specific suppressive factor in order to provide a satisfactory antigenic for producing antibody to the non-specific suppressive factor by conventional animal immunization techniques or by the hybridoma techniques of Kohler and Milstein. Such antibodies can be tagged with radioactive labels, such as iodine, technetium-99m or the like or fluorescent markers of other conventional tags to provide an assay means for measuring the level of non-specific suppressive factor in a patient's blood serum. Furthermore, such antibodies would be useful for treating the patient's plasma to provide contact between the antigen and antibody thereby to effect antigen removal from the plasma by antigen-antibody interaction. In addition, the purified non-specific suppressive factor is useful in treating patients afflicted with a disease associated with an overactive immunosuppressive condition such as rheumatoid arthritis, multiple sclerosis, severe allergy or lupus.

SUMMARY OF THE INVENTION

This invention provides a hitherto unknown form of high purity non-specific immunosuppressive factor (IF) which is stable including being highly stable in dilute aqueous solutions. It is isolated by a chromatographic procedure and can be isolated in its pure form or in admixture with a protein composition which is inert with respect to its stability characteristics. In the process of this invention, human ascites fluid are delipidated and are subjected to chromatography in a first separation step. The IF-rich fraction obtained contains stable IF having a molecular weight of about 50,000 and inert proteinaceous material which does not degrade the IF. Pure stable IF having a molecular weight of about 50,000 is obtained by contacting the IF-rich composition with anti-human IgG (Fc specific) immunosuppressive. The stable IF-rich fraction or the pure stable IF fraction is useful for producing antibody to IF or it can be further reduced to low molecular weight IF having a molecular weight of about 25,000 by dissociation with 3.5 magnesium chloride and separating on Sephacryl S-200 column which is also very active as a non-specific immunosuppressive factor.

DETAILED DESCRIPTION OF SPECIFIC EMBODIMENTS

Figure 1:
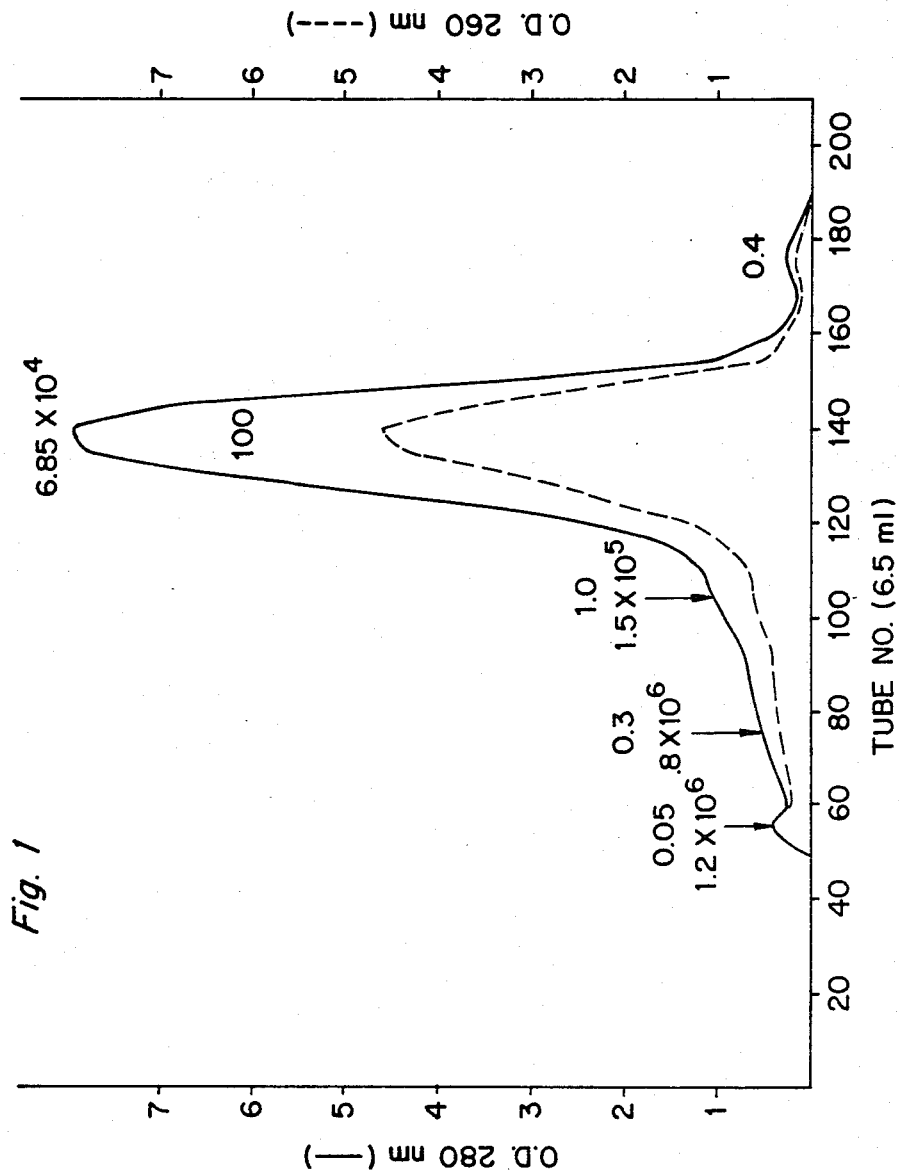

The immunosuppressive moiety of this invention is an acidic protein of isoelectric point below 4.0 with the minimum M.W. of 25,000. Its relatively small M.W. (50,000 under non-reducing conditions; 25,000 under reducing conditions) distinguishes it from the other large M.W. serum suppressive factors such as low density lipoprotein inhibitor, $\alpha$2-macroglobulin or pregnancy associated lipoproteins. Non-detectable involvement of carbohydrate as assessed by various lectin affinity media as well as peridoate Schiff's staining of the isolated component on polyacrylamide gel, further distinguishes from the numerous acute phase reacting glycoproteins such as $\alpha$1-acid glycoprotein, $\alpha$-fetoprotein, C-reactive protein or interferon. Non-dialyzable, acidic nature of this factor also differs from other peptide factors such as fibrinogen degradation products, serum amyloid protein and other small M.W. cytotoxic peptide factor or interferon. Thus, this suppressor factor is a unique component in plasma previously unidentified. Although anti-human thymocyte serum or anti-normal human serum reacts with this substance and removes its suppressive property, it does not react with monoclonal antibodies directed to non-polymorphic HLA antigen or HLA-DR antigen. In addition, this suppressor cross reacts with monoclonal antibody directed against sheep erthrocyte receptors on human peripheral T cells and appears therefore, to be related to these receptors. The evidence for this is: (1) SDS-PAGE analysis of immune complexes formed between monoclonal antibody and partially purified suppressor preparation reveals that the antibody is reacting with the non-immunoglobulin component of the preparation. (2) Purified suppressive factor inhibits SRBC rosette formation by peripheral blood T lymphocytes, consistent with a competition between the suppressor and receptors on T cells. (3) Immunosuppression can be reduced by absorption with monoclonal antibody directed to sheep erythrocyte receptors. (4) Immunosuppressive activity can be removed by absorption with sheep erythrocytes. Absorption of the suppressive activity with human erythrocytes is poor and absorption with rabbit erythrocytes does not remove any of the suppressive activity at all. These results are consistent with observations that only a small portion (5-10%) of E-rosette forming cells (E-

RFC) form rosettes with human erythrocytes and that rabbit erythrocytes do not form any rosettes with human peripheral blood lymphocytes.

The fact that even the partially purified suppressive factor universally suppresses the PHA response of the donor lymphocytes regardless of HLA or HLA-DR types and that sheep erythrocyte receptors are uniformly distributed on peripheral blood T lymphocytes show that the presence of this suppressor factor is not likely to be genetically restricted. Therefore, it differs from the soluble T cell MLC suppressor factor described by Engleman et al (J. Exp. Med. 147:1037), which shows genetic restriction in the HLA-DR region.

The IF of this invention is derived from human ascites fluid, serum of cancer patients or Cohn fraction IV. The ascites fluid, from malignant or benign disease, cirrhotic liver disease or bovine serum is delipidated to remove very low density and low density lipoproteins by contact with phosphotungstic acid and magnesium chloride. The delipidated solution then is dialyzed to remove the treating acid and salt and its pH is then adjusted to between about 5.5 and 6.5, preferably about 6 by addition of phosphoric acid, possibly other weak acids or the like.

The solution then is fractionally precipitated by salt precipitants such as with ammonium sulfate or sodium sulfate and then passed through a chromatographic column of a resin which does not degrade protein molecules and which is equilibrated with the salt solution used to dissolve the ammonium sulfate precipitate of IF. The extract is separated into its components within the column. The column then is eluted in a conventional manner with an aqueous salt solution to recover the individual fractions. The IF-rich fraction contains a proteinaceous composition which does not adversely affect the stability of the IF. That is, the IF separated within the column is not subjected to enzymatic or proteolytic degradation in contrast to the IF in its natural state. In order to minimize IF degradation which occurs in the natural state prior to processing in accordance with the present invention, the ascites fluid preferably are cooled to a temperature between about 1° C. and 5° C., preferably about 4° C.

Suitable resin compositions that can be utilized in the gel filtration chromatography step are ACA-22 (2% each of agarose and acrylamide cross-linked gel), Sepharose 48 or Biogel 0.5 m or the like.

Since the IF fraction recovered by gel filtration chromatography contains an inert proteinaceous material, it must be treated further in order to isolate the IF. Occasionally, it is preferable to use Concanavalin A-Sepharose column chromatography prior to solid phase anti-IgG column chromatography. This removes α2-macroglobulin and IgM contaminants. The fraction determined to have activity as IF and having a molecular weight of about 50,000 is contacted with an anti-human IgG Fc specific immunoadsorbent which is produced in an animal such as sheep, goat, rabbit or cow or the like. This contact is effected by repeated passage through anti-IgG column until no more change in absorption at 280 nm takes place, 5×normally. Other suitable immunoadsorbents include IgG SORB which is fixed Staphylococus aurens strain Cowan II protein A. This step is necessary because IF is associated with aggregated immunoglobulin G and Cig.

The IF of this invention is useful as treating sera for treating a deficiency of the IF activator to animals. The IF also is useful in producing IF antibody by injecting it into the blood circulation system of a goat, horse, rabbit, chicken or other animals normally used for producing sera. After a suitable incubation period, the blood is removed from the animal and centrifuged to recover the blood serum from which the antibodies to the IF are contained.

EXAMPLE I

Preparation of Serum and Ascites Fluids

Serum was prepared from normal citrated human plasma (obtained from the Red Cross Blood Bank, Boston, MA) by the addition of one volume of calcium chloride solution (16 g $CaCl_2.2H_2O$/100 ml of $H_2O$) to 100 volumes of plasma, followed by incubation for one hour at 37° C. and overnight at 4° C. The fibrin clot was disrupted with a glass rod and the released serum was filtered through three layers of cheese cloth. Sterile ascites fluids were obtained from cancer patients who had not been on any chemotherapy and were centrifuged for 30 minutes at 2,000×g in order to remove intact cells. 500 ml aliquots were stored at −20° C. without any preservatives. Prior to chromatography, both pooled normal human sera and ascites fluids were centrifuged at 10,000×g for 30 minutes in order to remove cell debris and residual fibrin clots. Protein concentrations of the test samples were determined by the method of Bradford using a solution of human serum albumin as a standard (1 mg/ml).

Partial Delipidation of Ascites and Sera

The stepwise delipidation method described by Burstein et al (J. Lipid Res., 11:583) was used. Briefly, ascites fluid or serum were partially delipidated with 1/10 volume of 4% phosphotungstic acid and 1/40 volume of 2M magnesium chloride and centrifuged at 6,000×g for 10 minutes in order to remove the very low and low density lipoproteins. Excess phosphotungstic acid and magnesium ion were removed by dialysis against phosphate buffered saline (PBS; 0.15M sodium chloride and 0.01M phosphate buffer, pH 7.4) until the saline control, treated in the same manner as the test sample, did not exhibit any suppressive activity.

Gel Filtration Chromatography on ACA-22 Columns

Partially delipidated ascites fluid was adjusted to pH 6.0 with 1M phosphoric acid and the proteins were precipitated with ammonium sulfate at 50% saturation. The supernatant was removed by centrifugation at 20,000×g for 30 minutes and the precipitates were redissolved in a small volume (Ca 20 ml) of water and dialyzed against PBS overnight at 4° C. The resulting precipitates were removed by centrifugation and the supernatant fraction was chromatographed on an ACA-22 column (5×65 cm) (LKB instruments) which had been previously equilibrated with PBS at 4° C. Protein fractions were eluted with PBS at a flow rate of 45 ml per hour.

Preparative Flat Bed Isoelectrofocusing

Aliquots of protein to be separated by isoelectrofocusing were labelled with I-125 (Specific activity 17 Ci/mg, New England Nuclear, Boston, MA) to a specific activity of about $20 \times 10^6$ cpm/mg of protein using the solid phase lactoperoxidase technique of David and Reisfeld (Biochemistry, 13:1014). 20 to 100 mg of unlabelled protein was mixed with about $10 \times 10^6$ cpm of I-125 labelled material, further mixed with 150 ml of preswollen Bio-lyte electrofocusing gel (Bio-Rad Lab., Richmond, CA) and formed into a semi-solid block ($10 \times 22 \times 0.5$ cm). A pH gradient was produced with an equal volume mixture of 20% ampholytes of pH 2.5–4.0 and 40% of ampholytes of pH 4.0–6.0 at a final concentration of 1.5% ampholyte in the media. The electrofocusing block was placed over a cooling water bath, maintained at 20° C. and prefocused for 2 hours at 100 volts. Electrofocusing was performed at a constant voltage of 200 volts until minimum amperage was reached (usually 15–20 hours). At the end of the run, 1 cm sections were cut and eluted with 10 ml of water in order to measure the pH gradient. Each section was further eluted with 10 ml of PBS twice more and the distribution of radioactivity and the absorbance at 280 nm were monitored with an aliquot from each eluate. Each eluate was neutralized and dialyzed against PBS prior to assay for suppressive activity.

Immunoabsorption and Immunoprecipitation

Anti-human thymocyte serum was obtained from the Upjohn Company (Kalamazoo), MI) and IgG SORB was obtained from Tufts Enzyme Center (Boston, MA). Goat anti-human IgG (Fc specific) was obtained from Calbiochem (La Jolla, CA). Bovine anti-$\beta$2-microglobulin antiserum was obtained from Scripps Clinic and Research Foundation (La Jolla, CA). A crude gamma globulin fraction was obtained from each antiserum by precipitation with 18% sodium sulfate at room temperature. The precipitates were centrifuged at $20,000 \times g$ for 30 minutes and were resuspended in a minimum volume of water and dialyzed against PBS overnight at 4° C. Approximately 10 mg of protein was conjugated per ml of packed Sepharose 4B beads with the cyanogen bromide activation method of Cuatrecasas (J. Biol. Chem. 245:#12:3057). Excess active sites were saturated with glycine in PBS prior to the use of the immunoadsorbents. Antigen was absorbed with solid phase immunoadsorbent at 4° C. overnight on a rotating mixer. Unadsorbed material was removed by aspiration of the supernatant after centrifugation at $1,000 \times g$ for 15 minutes. The bound material was eluted with 3.5M magnesium chloride as suggested by Kessler (A.J. Imm. 115, #6:1617). Both the unbound and bound materials were tested for their activity in vitro. Monoclonal antibodies to non-polymorphic HLA-ABC antigen (W6/32) and HLA-DR antigen (MAS 019b) were obtained from Accurate Chemical and Scientific Corp. (Hicksville, NY). Monoclonal antibody to T cells was obtained from New England Nuclear (Boston, MA) which detects >99% of peripheral T cells and possesses specificity directed against sheep erythrocyte receptors (Kamoun et al, J. Exp. Med. 153:207). Immune complexes formed with monoclonal antibody were removed by the IgG SORB prior to testing for the residual suppressive activity. They were then eluted with 2% SDS for 2 minutes in a boiling water bath and analyzed on SDS-PAGE according to the procedure described by Oppermann et al (Cell, 12:993).

SDS-Polyacrylamide Gel Electrophoresis (PAGE)

SDS-PAGE was run according to the method of Fairbanks et al (Biochemistry, 10:2602) on 8% gels. I-125 labelled samples were reduced with 5% 2-mercaptoethanol for 30 minutes at 56° C., in 0.04M Tris-acetate buffer (pH 7.4) containing 1% SDS and 8M urea, which had been freshly deionized through a mixed bed resin, Rexyn I-300 (Fisher Scientific). Samples were also more rigorously reduced with 5% 2-mercaptoethanol in the presence of 2% SDS containing the same buffer as the above, in a boiling water bath for 2 minutes. At the end of the electrophoresis, gels were sliced with a gel slicer (Bio-Rad Lab.) and monitored for radioactivity on an automotive gamma counter, Model 5130 (Packard Instruments). I-125 labelled human immunoglobulin was used as a M.W. marker.

Double Immunodiffusion and Immunoelectrophoresis

Goat anti-normal human serum was obtained from Meloy (Springfield, VA) and all the other antisera made against human plasma proteins were obtained from Calbiochem (La Jolla, CA). Double immunodiffusion was performed in 1% Seakem agarose (Marine Colloids, Rockland, ME) prepared in 0.05M sodium barbital buffer (pH 8.6) containing 0.03% sodium azide. Immunoelectrophoresis was performed in the same agarose at 20° C. for 2 hours at 10 volts/cm of the plates.

Immunosuppressive Activity Assay In Vitro

Inhibition of the human lymphocyte proliferative response to phytohemagglutinin (PHA) was employed as an in vitro assay to assess immunosuppressive potency (Cooperband et al, Transpl. Proc. 1:516 and J. Clin. Inves. 47:836). Lymphocytes were prepared from freshly drawn blood from healthy donors using a Ficoll-Hypaque (Pharmacia Fine Chemicals, Piscataway, NJ) gradient or Lymphocyte Separation Medium (LSM, Litton Bionetics, Rockville, MD). $5 \times 10^6$ lymphocytes were suspended per ml of Eagle's minimal essential medium (MEM) containing Earle's salts, 100 units of penicillin per ml, 100 $\mu$g of streptomycin per ml, 2 mM L-glutamine, 10% heat inactivated fetal calf serum and optimal concentration of PHA-M (5.3 ug/well) (Difco Lab., Detroit, MI). 50 ul of lymphocyte suspension was used per test. Test samples were sterilized through 0.45 $\mu$m Millipore filters (Millipore Filter Corp., Bedford, MA) and varying concentrations of each sample (5~50 $\mu$l) were tested in quadruplicate in a total volume of 200 $\mu$l per well. Remaining volume was made up with the above culture medium. The viability of lymphocytes was examined by trypan blue dye exclusion at the end of their exposure to test samples in the absence of PHA. Cells were pulsed with 3H-thymidine (0.5μCi/0.25×10⁶ cells) (New England Nuclear, Specific activity 2 Ci/mM) 2 days after the initiation of PHA stimulation and harvested 24 hours later on a Titer Tech cell harvester (Litton Bionetics, Rockville, MD). Incorporation of 3H-thymidine into DNA was measured by counting the radioactivity on the filter discs in 5 ml of Scintilene (Fisher Scientific) using a Beckman liquid scintillation counter (Model LS-200). Concanavalin A (Miles Laboratories) and Pokeweed mitogen (Difco Lab.) responses were tested in a similar manner to that used for the PHA response. Percent suppression of DNA synthesis versus protein concentration of the test sample was plotted on graph paper and the protein concentration that resulted in 50% suppression of the control PHA response was calculated from this graph ($SD_{50}$). Specific activity of the suppressive factor was expressed as the $SD_{50}$ units per mg of protein. Mixed lymphocyte cultures were established at a final concentration of 0.5×10⁶ lymphocytes per well derived from two separate individuals. The cultures were pulsed with 3H-thymidine from day 5 to day 6. Incorporation of 3H-thymidine into DNA was measured in a similar manner to that used to measure mitogen responses. Synthesis of protein and RNA were measured after pulsing the plate with 3H-amino acid mixture (NET-250 New England Nuclear, Boston, MA), 0.625 μCi/well, and ³H-uridine (Specific activity; 20 Ci/mM, (Schwarz/Mann, Orangeburg, NY), 0.5 μCi/well from the beginning of the culture. Cultures were harvested on the third day and the synthesis of RNA was measured in a similar manner to that used for DNA. For the measurement of protein synthesis, cultures were transferred to glass test tubes and proteins were precipitated with 20 μl of 50% trichloroacetic acid (TCA) per well. Pellets were washed two times with 10% TCA and redissolved in 200 μl of NCS tissue solubilizer (Nuclear Chicago, Des Plaines, IL) and placed in 5 ml of aquasol (New England Nuclear, Boston, MA) for measurement of radioactivity on a Beckman liquid scintillation counter.

Assay for Natural Killer Cell Activity

⁵¹-Cr-labelled K562 cells were used as target cells and human peripheral blood lymphocytes were used as effector cells (prepared in the same manner as those prepared for the in vitro immunosuppressive activity assay (West et al, J. Imm., 118, 355–361). Quadruplicate cultures were established in round bottom microtiter plates in a total volume of 200 μl. Effector cells were added in 100 μl of medium to give effector/target (E/T) cell ratios of 50:1, 25:1 and 12.5:1. A constant number of ⁵¹Cr-labelled K562 cells (1×10⁴) were added to each well in 50 μl medium. The remaining volume in each well was brought to 200 μl with RPMI 1640+10% fetal calf serum, purified suppressor factor or equivalent volumes of PBS. The cultures were incubated at 37° C. in 5% incubator for 4 hours and the cell free supernant was counted for the released chromium in a Beckman Biogamma counter.

% cytotoxicity =

$$\frac{\text{Experimental }^{51}\text{Cr release} - \text{spontaneous }^{51}\text{Cr-release}}{\text{total }^{51}\text{Cr counts} - \text{spontaneous }^{51}\text{Cr release}} \times 100$$

In all experiments, spontaneous ⁵¹Cr release was measured with target K562 cells alone. Addition of purified suppressor factor to K562 cells did not result in any observable toxicity, as measured by trypan blue dye exclusion, and by its failure to increase the release of radioactivity from the cells.

Inhibition of Sheep Erythrocyte (E) Rosette Formation

The inhibition of sheep erythrocyte binding to lymphocytes was assayed in a manner similar to that described by Bach and Dardenne (Cell. Immunol. 3:1): 2×10⁶ lymphocytes in a total volume of 0.2 ml of Hank's balanced salt solution (HBSS) were mixed with 0.2 ml of a 1% suspension of sheep erythrocytes. 100 μl of the sample being tested was added to this mixture, which was then centrifuged at 400×g for 5 minutes, and further incubated for 16–20 hours at 4° C. The cell pellets were resuspended gently and examined microscopically for rosettes in which a single lymphocyte was surrounded by four or more sheep erythrocytes.

Absorption of Suppressor Factors with Erythrocytes

Absorbing erythrocytes were extensively washed with PBS (5×) and made to ghosts by hypotonic lysis with 10 times volume of water. One ml of packed erythrocyte ghosts prepared with sheep, human and rabbit blood was used per ml of test material at 4° C. overnight. Absorbed material was recovered from the supernatant after centrifugation at 20,000 rpm, 15 min for residual suppressive activity in vitro.

Immunosuppressive Activity In Vivo

Materials which suppressed human lymphocyte proliferation responses in vitro were subsequently tested for their ability to suppress T cell dependent antibody synthesis in vivo using a modified Jerne Hemolytic plaque assay (Glasgow et al, Proc. Exp. Biol. Med., 138:753). Briefly, adult $BDF_1$ mice (C57BL/6J×DBA/2) were injected i.v. with 0.5 ml of test sample 24 hours prior to immunization with 5×10⁸ sheep erythrocytes (SRBA), horse erythrocytes (HRBC) or chicken erythrocytes (CRBC). Mice were sacrificed 4 days after the injection of erythrocytes and the number of direct plaque forming cells per spleen was determined.

RESULTS

Delipidation and Salt Fractionation of Ascites and Sera

Partial delipidation of ascites or sera do not remove the suppressive activity. Therefore, these fluids are routinely delipidated prior to further fractionation. Precipitation with ammonium sulfate at 50% saturation at pH 6.0, recovers about 75% of the total suppressive activity in the precipitate.

Gel Filtration Chromatography on ACA-22 Column

Ammonium sulfate precipitated, crude suppressive material was fractionated on an ACA-22 column in PBS. A typical elution profile obtained from an ovarian cancer ascites fluid is shown in FIG. 1. The $SD_{50}$ and the percent distribution of suppressive activity of individual fractions are shown in Table 1. A very similar elution profile is seen with normal human plasma, although the quantity of Peak 1 material ($ACA_1$) was considerably smaller (5 mg of $ACA_1$ from 100 ml of plasma vs. 20–50 mg of $ACA_1$ from 100 ml of malignant ascites fluids). Double immunodiffusion against anti-human IgG indicates that this large MW Peak 1 material contains IgG. Additional bands seen from $ACA_1$ preparations may represent different subclasses of IgGs than that used in well #1 or some other modified forms of IgGs.

Anti-Human IgG Immunoadsorbent Chromatography $ACA_1$ preparation was further purified on a goat anti-human IgG (Fc specific) immunoadsorbent. A summary of this purification scheme is shown in Table 2. The suppressive activity was not removed by the anti-IgG immunoadsorbent. Rather, the adsorbent purified the suppressive factor by twenty-five fold.

Isoelectrofocusing Separation of ACA-22 Peak 1 ($ACA_1$)

Figure 2:
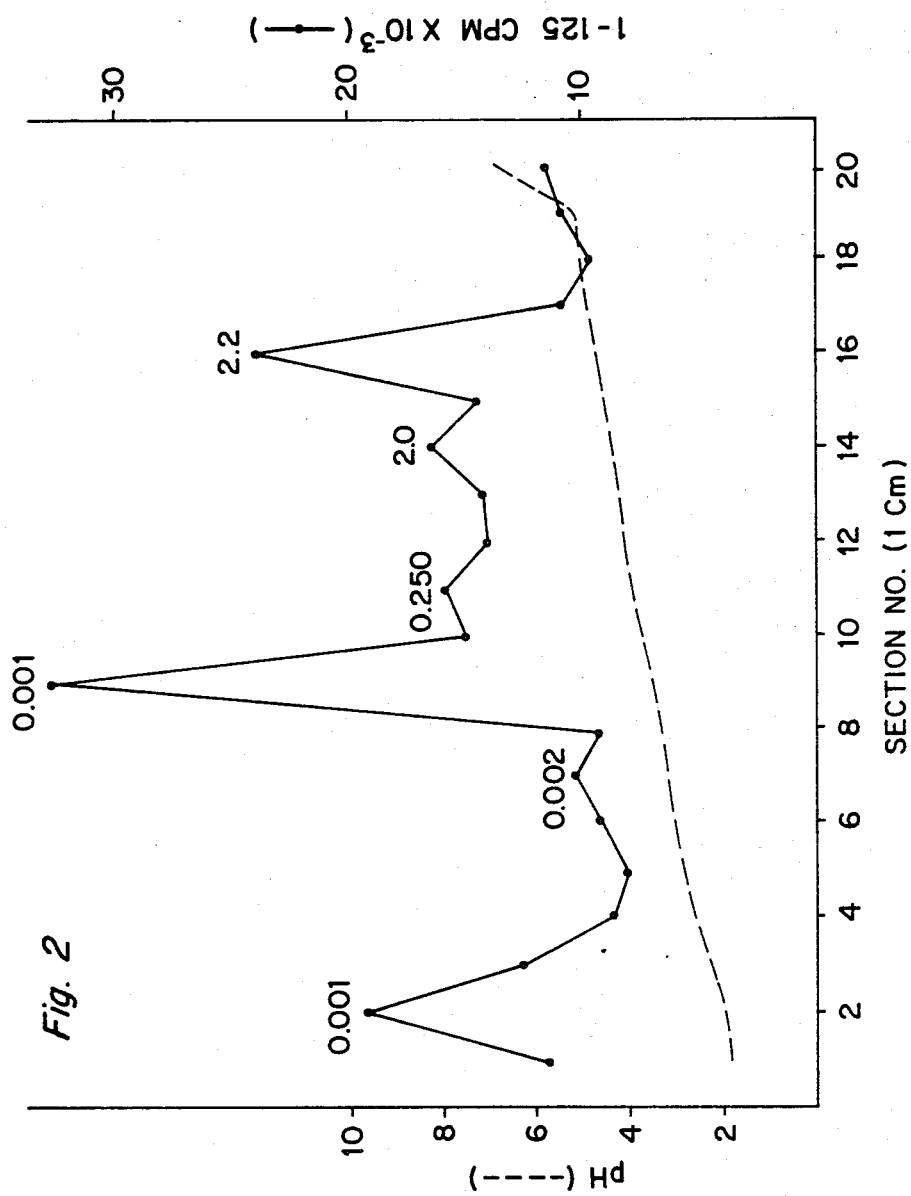

Isoelectrofocusing $ACA_1$ yielded the separation profile shown in FIG. 2. An active peak was seen at pH 2.6, similar to a component previously found after acid extraction of high molecular weight suppressive material, isolated from malignant ascites. However, other species of suppressive moieties were also demonstrated as shown in FIG. 2. Thus, components obtained at pH 2.0, 3.2 as well as at 3.6 all exhibited potent suppressive activity without any cytotoxicity to target lymphocytes as determined by trypan blue dye exclusion.

SDS-PAGE Analysis of the $ACA_1$ Suppressive Component

Figure 3:
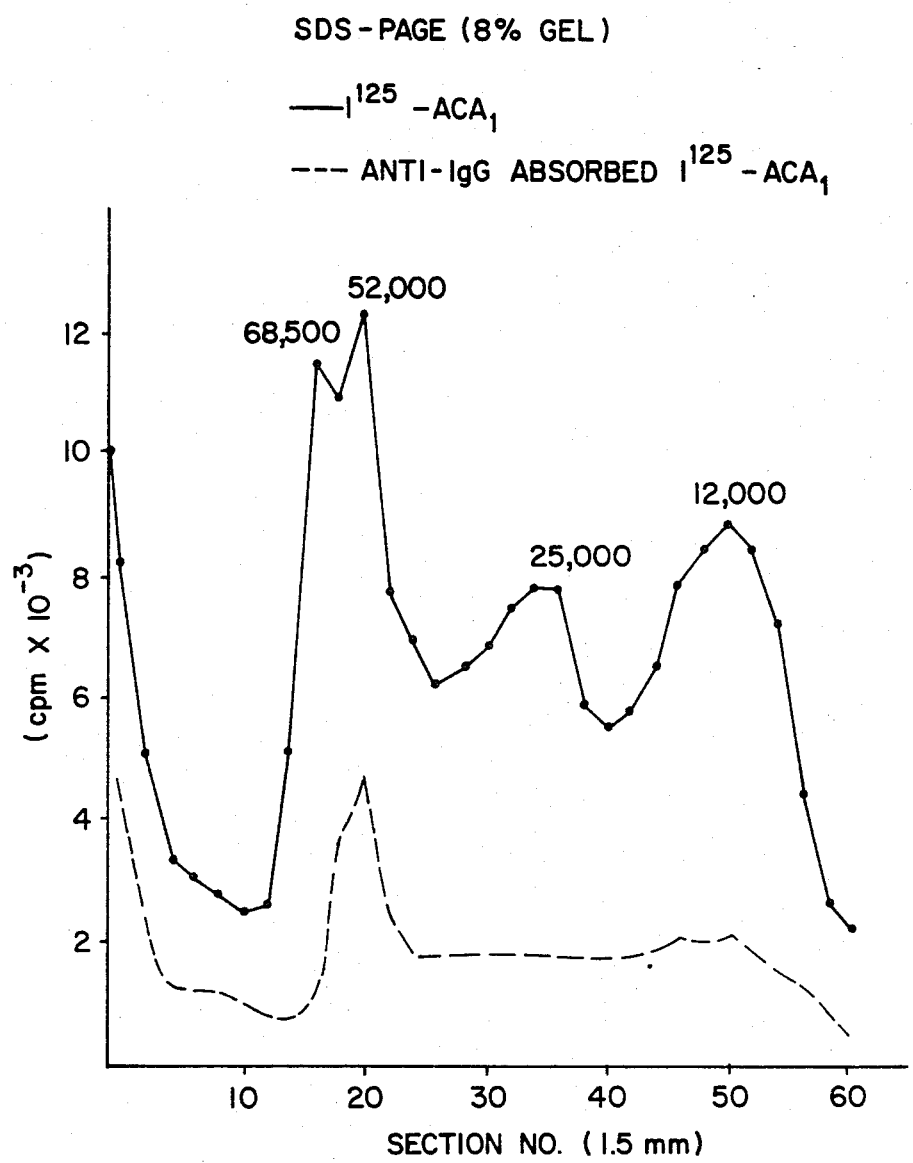
Figure 4:
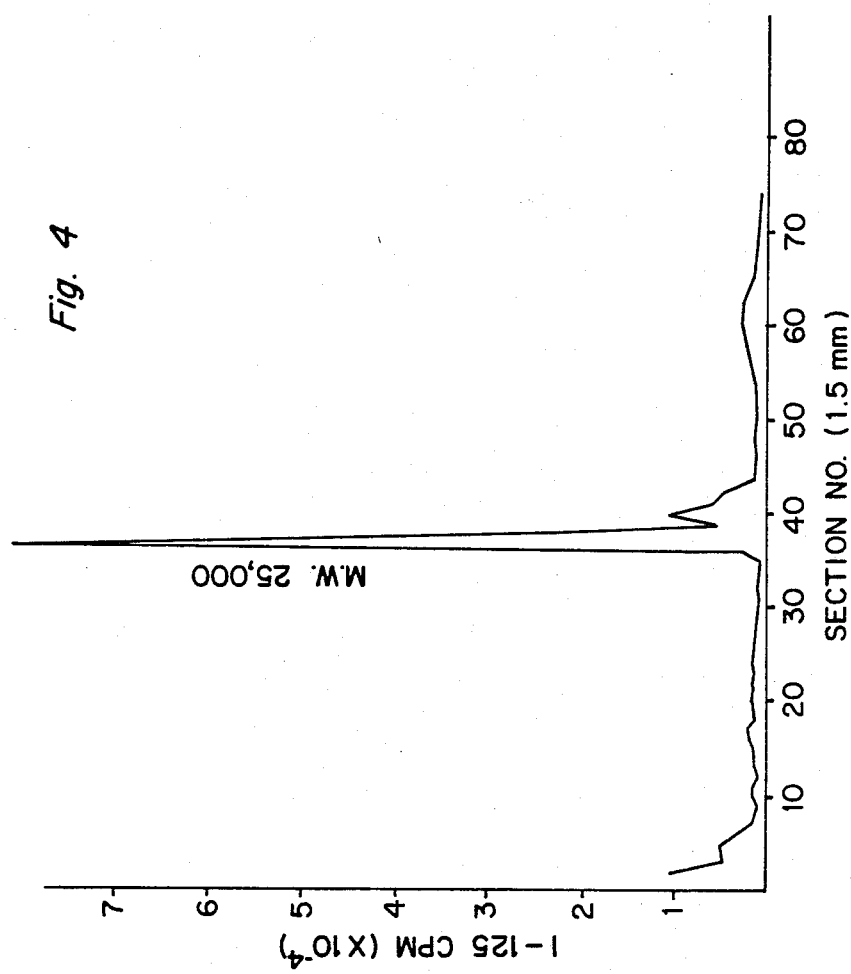

In order to gain an insight into the nature of the $ACA_1$ complex, $ACA_1$ preparations were labelled with I-125 and analyzed on SDS-PAGE before and after absorption with an antihuman IgG immunoadsorbent as shown in FIG. 3. Completeness of absorption was assured by the lack of reaction with the antiserum on Ouchterlong double immunodiffusion or immunoelectrophoresis. The only component left after absorption with anti-IgG was of M.W. 50,000 as assessed by Fairbanks' SDS-PAGE analysis. A similar component was observed upon dissociation of immune precipitates obtained with antithymocyte serum and $ACA_1$. Under more rigorous reducing conditions (2 minutes in a boiling water bath), this same component exhibits a M.W. of 25,000. SDS-PAGE analysis of the immune complexes produced with monoclonal antibody to sheep erythrocyte receptor of T cells and the $ACA_1$ preparation reveals the same M.W. 25,000 component as seen on FIG. 4. Thus, it appears that the $ACA_1$ preparation contained a component immunologically similar to the sheep erythrocyte receptor of peripheral T cells. Evidence that this component is responsible for at least part of the immunosuppressive activity of $ACA_1$ preparation is described below.

Effect of Antisera to Human Plasma Proteins and Human Thyrocytes on the Suppressive Activity of $ACA_1$ $ACA_1$ preparations were absorbed with various solid phase immunoadsorbents and the residual suppressive activity was tested. Table 3 shows that the immunoadsorbent made with anti-normal human serum as well as human thymocyte serum removed substantial amounts of suppressive activity from $ACA_1$ preparations, whereas those of anti-IgG (Fc specific), IgG SORB and anti-$\beta$2-microglobulin did not remove any suppressive activity. Therefore, the immunosuppressive activity must reside in the non-immunoglobulin portion of the complexes. Of particular interest was the observation that an anti-human thymocyte immunoadsorbent almost completely removed the suppressive activity of the $ACA_1$ preparation. This finding suggested that the suppressive activity of the $ACA_1$ preparation must reside in a component of thymocytes. To test this further, $ACA_1$ was reacted with monoclonal antibody directed against sheep erythrocyte receptors of human peripheral T cells (supplied by New England Nuclear Co.) and the resulting immune complex was removed with IgG SORB. Residual suppressive activity was tested by in vitro assay. Removal of the complexes was necessary, since the monoclonal antibody, if left in the culture, interferes with subsequent stimulation by phytohemagglutinin. As shown in Table 4, the monoclonal antibody significantly reduces the suppressive activity of $ACA_1$ preparations. However, suppressive activity cannot be totally abrogated even with 20 times of antibody used in this experiment. This may be due to incomplete removal of antibody which exerts immunosuppressive effect (compare monoclonal antibody+IgG-SORB with IgG-SORB alone in Table 4) or there may be another immunosuppressor molecule which does not react with the monoclonal antibody.

As a further means of ascertaining the extent to which the suppressive activity in the $ACA_1$ preparation was related to SRBC receptors of T cells, two additional experiments with SRBC were performed. Table 5 shows that this purified suppressor factor also inhibits sheep erythrocyte rosette formation at microgram concentrations per ml. Table 6 shows that sheep erythrocyte can absorb the suppressor factor and remove its suppressive activity, confirming that the suppressor factor does recognize sheep erythrocytes. In contrast, human erythrocytes only partially removed the suppressive activity and rabbit erythrocytes did not remove any suppressive activity at all.

Immunosuppressive Properties of Suppressive Factor In Vitro

Figure 5:
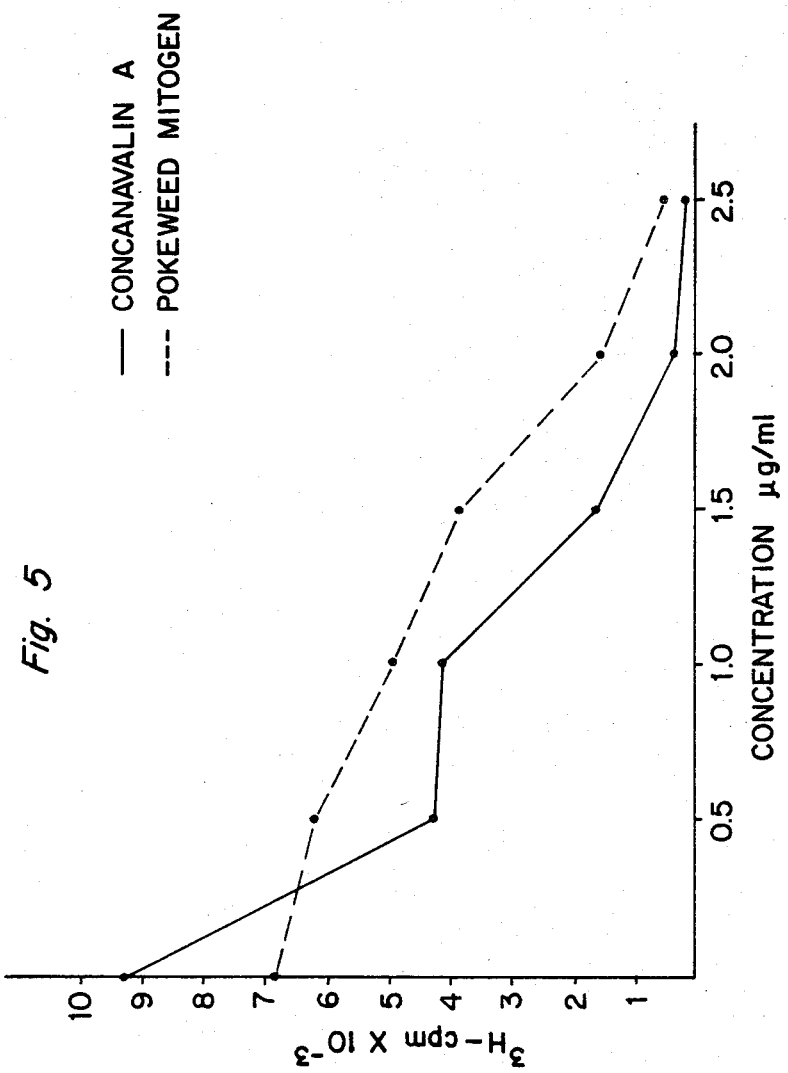

The purified suppressive factor exerts a potent immunosuppressive effect on two way mixed lymphocyte culture reactions (MLC). It inhibits 100% of MLC at 15 $\mu$g/ml respectively. As shown in FIG. 5 both concanavalin A (Con A) and pokeweed mitogen (PWM) responses were similarly inhibited by the suppressor factor. Table 7 shows that both DNA synthesis and, to a lesser extent, RNA synthesis were inhibited by the suppressor factor, resembling responses to the inhibitors of DNA synthesis (IDS) described by Namba et al (J. Immunol., 118, #4:1379). Protein synthesis was not inhibited and in fact may have been slightly stimulated by the presence of suppressor factor. This suppressor factor also inhibits natural killer cell activity by 78% at 1.0 µg/ml concentrations on all the effector to target ratios (50:1, 25:1 and 12.5:1).

Immunosuppressive Activity of Suppressor Factor In Vivo

Figure 6:
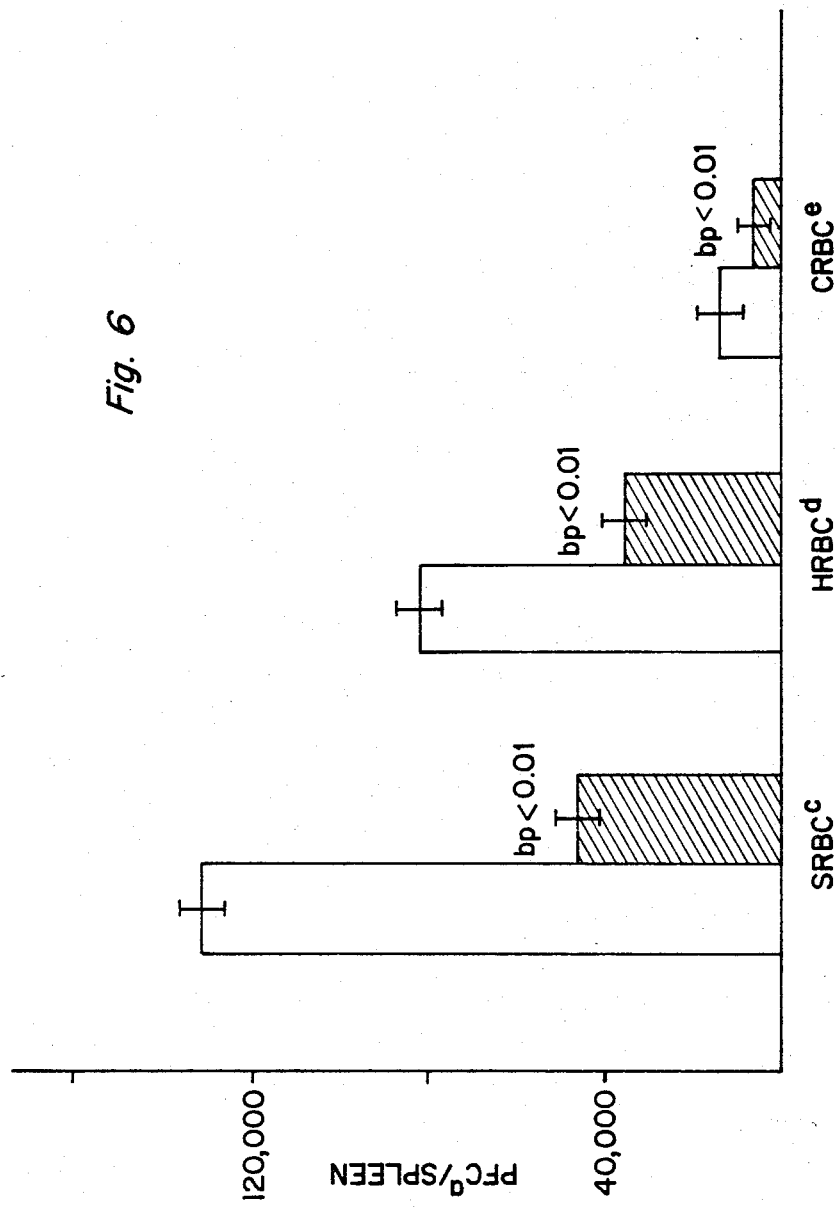

Table 8 shows that purified suppressor factor exhibits potent immunosuppressive effect on plaque forming cell response to sheep erythrocytes. FIG. 6 indicates that the suppressive property is not limited to sheep erythrocyte response along but is almost equally effective against horse and chicken erythrocytes as well.

TABLE 1

Protein and Activity Distribution of ACA-22 Chromatographic Fractions

| | Tube No. | $SD_{50}{}^a$ | mg Protein | % Activity |
|---|---|---|---|---|
| Fraction 1 ($ACA_1$) | 50–60 | 0.05 | 26 | 49.9 |
| Fraction 2 ($ACA_2$) | 61–93 | 0.30 | 114 | 35.9 |
| Fraction 3 ($ACA_3$) | 94–120 | 1.00 | 101 | 9.5 |
| Fraction 4 ($ACA_4$) | 121–165 | 100.00 | 2193 | 2.1 |
| Fraction 5 ($ACA_5$) | 166–190 | 0.40 | 15 | 3.5 |

[a]Defined as the protein concentration (µg/ml) which suppresses the control PHA responses by 50%.

TABLE 2

Purification Scheme

| | $SD_{50}{}^a$ | Protein (mg) | % Activity Recovered |
|---|---|---|---|
| Delipidated Whole Ascites | 4.0 | 6500 | 100 |
| 50% Sat. Ammo. Sulfate Ppt. | 2.0 | 2392 | 73.6 |
| ACA-22 Peak 1 ($ACA_1$) | 0.05 | 26 | 32 |
| Anti-IgG Seph. Unbound | 0.002 | 1.0 | 31 |

[a]Defined as the protein concentration (mg/ml) which produces 50% suppression of the control PHA response.

TABLE 3

Effect of Various Antisera on The Suppressive Activity of $ACA_1$

| | CPM | (% Suppression)[a] |
|---|---|---|
| Unstim. | 207 ± 25[b] | |
| PHA Stim. | 29,835 ± 1,843 | |
| $ACA_1$ alone | 1,724 ± 286 | (95.0) |
| $ACA_1$:Anti-$ACA_1$ (1:50)[d] | 20,230 ± 1,481 | (32.4) |
| $ACA_1$:Anti-NHS[e] (1:50) | 25,635 ± 946 | (14.2) |
| $ACA_1$:ALS[f] (1:50) | 28,474 ± 1,431 | (4.7) |
| $ACA_1$:NRS-IgG[g] (1:50) | 3,993 ± 286 | (87.2) |
| $ACA_1$:Anti-IgG (1:50) | 1,643 ± 455 | (95.3) |
| $ACA_1$:IgG SORB[h] (1:400) | 2,375 ± 227 | (93.0) |

[a]Residual suppressive activity
[b]Mean ± S.E.
[c]Ratio of protein used
[d]Anti-normal human serum
[e]Anti-lymphocyte serum
[f]Normal rabbit serum IgG
[g]Staphylococcal protein A immunoadsorbent

TABLE 4

Effect of Monoclonal Antibody to Sheep Erythrocyte Receptors on the Suppressive Activity of $ACA_1$

| $ACA_1$ (µg) | Ab (µg) | IgG SORB[a] (µl) | cpm[b] | (% suppression) |
|---|---|---|---|---|
| | | | Unstim. 240 ± 44 | |
| | | | PHA stim. 43,659 ± 1,538 | |
| 200 | 0 | 0 | 177 ± 39[c] | (100) |
| 200 | 0 | 200 | 274 ± 18 | (100) |
| 0 | 1 | 200 | 7,738 ± 2,935 | (82) $p < 0.01^c$ |
| 200 | 1 | 0 | 8,364 ± 1,133 | (81) $p < 0.01^c$ |
| 200 | 1 | 200 | 20,057 ± 2,024 | (56) $p < 0.01^{c,d}$ |
| 0 | 0 | 200 | 43,390 ± 1,896 | (0) |

[a]Staphylococcal protein A immunoadsorbent
[b]Mean ± S.E.
[c]Level of significance by student's test compared with control $ACA_1$ alone.
[d]Compared with IgG SORB and Ab column.

TABLE 5

Effect of the Suppressor Factor On Rosette Forming Cell Assay

| Anti-IgG absorbed $ACA_1$ Concentration µg/ml | $RFC^a/10^3$ cells[b] | % inhibition |
|---|---|---|
| 12.0 | 0 | 100 |
| 10.0 | 0 | 100 |
| 7.2 | 12.2 ± 3.7 | 94 |
| 4.8 | 30 ± 11 | 86 |
| 2.4 | 102 ± 18 | 53 |
| 1.2 | 132 ± 15 | 39 |
| 0 | 216 ± 20 | 0 |

[a]Rosette forming cell assay
[b]Mean ± S.E.

TABLE 6

Effect of Absorption with Erythrocytes on the Suppressive Activity of the Suppressor Factor In Vitro

| Samples Tested | $^3$H-thymidine $CPM^a$ after absorption | | | |
|---|---|---|---|---|
| | None | SRBC[b] | HRBC[c] | RRBC[d] |
| $ACA_1$ (2.5 mg/ml) | 1,323 ± 276 | 16,478 ± 233 | 3,325 ± 175 | 1,382 ± 113 |
| Purified suppressor factor (0.1 mg/ml) | 750 ± 157 | 18,665 ± 1,502 | 3,871 ± 178 | 978 ± 390 |
| PBS[e] control | 14,103 ± 592 | 20,340 ± 684 | 22,020 ± 690 | 20.774 ± 462 |

[a]Mean ± S.E.
[b]Sheep erythrocytes
[c]Human erythrocytes
[d]Rabbit erythrocytes
[e]Phosphate buffered saline

TABLE 7

Suppressive Property of the Purified Suppressor Factor On DNA, RNA and Protein Synthesis Induced by PHA

| | 3H-cpm incorporated (% suppression) | | |
|---|---|---|---|
| | DNA Synthesis | RNA synthesis | Protein synthesis |
| Unstim. | 871 ± 299 | 1,325 ± 147 | 23,672 ± 1,887 |
| PHA stim. | 42,168 ± 4,710 | 28,539 ± 994 | 35,104 ± 2,735 |
| Anti IgG absorbed $ACA_1$ | | | |
| 2.5 µg/ml | 791 ± 132 (100) | 10,980 ± 387 (62) | 41,618 ± 2,929 |
| 1.25 µg/ml | 19,397 ± 2,776 (54) | 14,408 ± 943 (50) | 39,328 ± 3,119 |
| 0.5 µg/ml | 34,799 ± 963 (18) | 18,133 ± 1,264 (36) | 31,598 ± 2,239 |

TABLE 8

In Vivo Assay of ACA$_1$ and Anti-IgG Purified ACA$_1$

| | PFC$^a$ - SRBC$^b$/Spleen | % Suppression |
|---|---|---|
| 10 mg BSA$^c$ | 214,200 ± 16,440 (6)$^d$ | 0 |
| 1.2 mg ACA$_1$ | 43,020 ± 3,900 (6) | 80.0 |
| 0.1 mg Anti-IgG$^e$ absorbed ACA$_1$ | 11,200 ± 2,400 (6) | 94.8 |

$^a$Plaque forming cell response as mean ± S.E.
$^b$Sheep erythrocytes
$^c$Bovine serum albumin, used as control protein
$^d$No. of animals used
$^e$Goat anti-human immunoglobulin G

I claim:

1. The process of obtaining a pure composition derived from human ascites fluid of a cancer patient or Cohn fraction IV having non-specific immunosuppressive factor activity and free of carbohydrate moities consisting of reduced immunosuppressive factor having a molecular weight of about 25,000, which composition is free from the components of immunosuppressive factor which degrade the immunosuppressive factor, said composition being reactive with anti-human thymocyte serum or anti-normal human, being non reactive with monoclonal antibodies to non-polymorphic HLA antigen or HLA-DR antigen, being cross-reacted with monoclonal antibody directed against sheep erythrocyte receptors on human peripheral T-cells, being absorptive with sheep erythrocyte and uniformly suppresses the PHA responsive donor lymphocytes regardless of HLA or HLA-DR and having an isoelectric point below about 4.0 which comprises forming a delipidated aqueous animal fluid containing immunosuppressive factor, precipitating the immunosuppressive factor by salt fractionation, passing said delipidated fluid through a gel filtration column resin to form a component rich in said immunosuppressive factor and substantially free of components of said ascites fluid that degrade said immunosuppressive factor, eluting said column with an aqueous salt solution to recover said component rich in immunosuppressive factor and contacting said component with anti-human IgG (Fc specific), recovering said pure composition and dissociating and separating said pure composition by column chromatography to obtain an active immunosuppressive factor having a molecule weight of about 25,000.

* * * * *